United States Patent [19]

Brocia

[11] Patent Number: 5,585,235

[45] Date of Patent: Dec. 17, 1996

[54] FLUORESCENT ASSAY AND METHOD THAT CORRECTS FOR SPECTRAL INTERFERENCE

[75] Inventor: Robert W. Brocia, Bronxville, N.Y.

[73] Assignee: Diagnescent Technologies, Inc., Yonkers, N.Y.

[21] Appl. No.: 148,731

[22] Filed: Oct. 29, 1993

Related U.S. Application Data

[63] Continuation-in-part of Ser. No. 46,772, Apr. 13, 1993.

[51] Int. Cl.$^6$ ............................ C12Q 1/00; C12Q 2/60; G01N 33/53

[52] U.S. Cl. ........................ 435/4; 435/7.92; 435/7.9; 435/11; 435/810; 435/975; 436/829; 436/809; 436/817; 514/2

[58] Field of Search .......................... 435/4, 11, 7.92, 435/7.9, 810, 975; 436/809, 807, 829, 817; 514/2

[56] References Cited

U.S. PATENT DOCUMENTS

| | | | |
|---|---|---|---|
| 4,366,244 | 12/1982 | Pascal | 435/11 |
| 4,677,057 | 6/1987 | Curtiss et al. | 435/7.92 |
| 4,883,765 | 11/1989 | Tamir et al. | 435/11 |
| 4,892,815 | 1/1990 | Kerscher et al. | 435/11 |
| 5,118,613 | 6/1992 | McGowan | 435/11 |
| 5,128,318 | 7/1992 | Levine et al. | 514/2 |
| 5,135,716 | 8/1992 | Thakore | 435/11 |
| 5,183,738 | 2/1993 | Adachi et al. | 435/11 |
| 5,217,873 | 6/1993 | Caris et al. | 435/11 |

OTHER PUBLICATIONS

Pattnaik et al, Biochimica et Biophysica Acta, 530(1987) pp. 428–438.

Dousset et al, Clinical Chem, vol 38, No. 2, 1992.

Nicols et al, J. Lipid Research, vol. 6, pp. 206–210 (1965).

Milner et al, Biochimica et Biophysica Acta, 1082 (1991) pp. 71–78.

Li et al, Jour of Lipid Research, vol. 33, pp. 503–512, (1992).

Craig et al, Jour. of Lipid Research, vol. 22, 1981, pp. 687–696.

Rye et al, Jour. of Lipid Research, vol. 33, 1992, pp. 215–224.

"Effect of Very Low–Density Lipoproteins on Lipid Transfer in Incubated Serum" by A. V. Nichols and L. Smith, *Journal of Lipid Research*, vol. 6, pp. 206–210 (1965).

"Cholesteryl Ester Exchange Protein in Human Plasma Isolation and Characterization" by N. M. Pattnaik, A. Montes, L. B. Hughes and D. B. Zilversmit, *Biochimica et Biophysica Acta*, 530, pp. 428–438 (1978).

(List continued on next page.)

*Primary Examiner*—John Kight
*Assistant Examiner*—Louise N. Leary
*Attorney, Agent, or Firm*—Lackenbach Siegel Marzullo Aronson & Greenspan, PC

[57] ABSTRACT

A method is provided for measuring the activity of cholesteryl ester transfer protein or MTP. The method comprises the steps of: adding a prepared emulsion particle to a buffer to form a buffered solution simulating physiological conditions, adding an emulsion of lipid to the buffered solution of prepared sonicated particle, adding a source of CETP or MTP to the buffered solution, adding a compound to the buffered solution for the purpose of testing the compound's effect on the neutral lipid transfer protein (CETP or MTP) activity, incubating the buffered mixture, reading the fluorescence of the solution, and calculating the effect of the compound on the emission spectra of the transfer label so transfer activity can than be accurately determined. A device that determines the activity of CETP or MTP by the use of a newly synthesized donor particle without regard to the presence of colored or otherwise interfering factors. A system comprises a donor particle comprised of a self quenching fluorescent neutral lipid core, an acceptor particle to accept protein facilitated transfer of fluorescent neutral lipid, and determining interference on the emission intensity of the fluorescence of the particles.

39 Claims, 7 Drawing Sheets

OTHER PUBLICATIONS

"Fluorescent Determination of Cholesteryl Ester Transfer Protein (CETP) Activity in Plasma" by N. Dousset and L. Douste-Blazy, *Clinical Chemistry*, vol. 38, No. 2, p. 306 (1982).

"Enhancement of the Human Plasma Lipid Transfer Protein Reaction by Apolipoproteins" by T. G. Milner, K. W. S. Ko, T. Ohnishi and S. Yokoyama, *Biochimica Biophysica Acta*, 1082, pp. 71–78 (1991).

"Use of Fluorescent Cholesteryl Ester Microemulsions in Cholesteryl Ester Transfer Protein Assays" by C. L. Bisgaier, L. L. Minton, A. D. Essenburg, A. White and R. Homan, *Journal of Lipid Research*, vol. 34, pp. 1625–34 (1993).

"Protein Disulfide Isomerase Is a Component of the Microsomal Triglyceride Transfer Protein Complex" by J. R. Wetterau, K. A. Combs, S. N. Spinner and B. J. Joiner, *The Journal of Biological Chemistry*, vol. 265, No. 17, pp. 9800–9807 (Jun. 15, 1990).

FLUORESCENT ASSAY AND METHOD THAT CORRECTS FOR SPECTRAL INTERFERENCE

RELATED APPLICATION

This application is a continuation-in-part of application Ser. No. 08/046,772 filed Apr. 13, 1993, still pending.

BACKGROUND OF THE INVENTION

1. Field of the Invention

The present invention relates to the field of drug development and, in particular, to a high volume screening process used to measure the effects of compounds on enzyme activity. The present invention is a method and device that eliminates the difficulties associated with the utilization of fluorescent methods in the presence of unknown compounds. More particularly, it is a fluorescent method that includes a synthetic particle for determination of neutral lipid transfer protein activity with provisions to correct for interference that would normally occur during the measurement of the activity, and is a device that carries out this method or test.

2. Description of the Prior Art

Neutral lipid transfer proteins include both cholesteryl ester transfer protein (CETP) and microsomal transfer protein (MTP). CETP is a protein that transfers cholesteryl ester (CE) from high-density lipoprotein (HDL) to low-density lipoprotein (LDL) and very-low density lipoprotein (VLDL). CETP will also transfer triglyceride (TG) among lipoprotein particles. For example, when a sample of VLDL or LDL, 1 or 10 micrograms of protein, respectively, is mixed with a sample of HDL, at total HDL cholesteryl ester of 4EE-10 moles, incubated at thirty seven degrees centigrade with a source of CETP, such as, one microliter of human plasma, cholesteryl ester will be transferred from the HDL to the LDL or VLDL particles.

MTP is an intra-cellular protein believed to be associated with the endoplasmic reticulum (ER) of normal liver and intestinal cells. MTP is also believed to be responsible for the synthesis and secretion of very low density lipoprotein (VLDL). If 100 microliters of liver cell homogenate is added to 4EE-10 moles of HDL cholesteryl ester and 1 ug of VLDL protein at 37 degrees centigrade for 12 hours, transfer of neutral lipid among the lipoproteins will occur.

Typically, the measurement of the CETP or MTP activity requires the cholesteryl ester associated with the HDL be provided with some type of label for monitoring movement of the HDL cholesteryl ester to the LDL and VLDL components after incubation. The activity measurement techniques also usually require a final separation step after incubation so that either accumulation of HDL cholesteryl ester in LDL or VLDL may be quantified, or loss of HDL cholesteryl ester from HDL may be quantified. The HDL particle represents a donor of CE, and the VLDL or LDL represent acceptors of CE.

There are several known techniques to measure cholesteryl ester transfer protein (CETP) activity. For example, an article entitled: Effect of Very Low-Density Lipoproteins on Lipid Transfer in Incubated Serum, by A. V. Nichols and L. Smith, J. Lipid Research, vol. 6, pp. 206–210 (1965), measures the activity of CETP by determination of cholesteryl ester (CE) mass transfer. The determination of CE mass transfer from high density lipoprotein to very-low density lipoprotein (VLDL) and low density lipoprotein (LDL) requires the re-isolation of VLDL and LDL after incubation with HDL and the CETP source in order to determine the cholesteryl ester mass transfer.

The VLDL/LDL re-isolation from the incubation mixture is a technique that includes ultra-centrifugation of the incubation mixture for many hours so that the VLDL and LDL components are floated upwards through a density gradient as the HDL component of the incubation mixture sinks to the bottom of the centrifuge tube. Further processing of the sample requires a method of determining the amount or mass of cholesteryl ester associated with the re-isolated VLDL or LDL and equating a change in mass to CETP facilitated transfer. Later variations of this method of activity measurement have simplified mass determination by utilizing HDL that has a radioactive label associated with the CE.

While not stated in this article, the determination of CETP activity through tritium (3H) labeled cholesteryl ester (3H-CE) still requires the time consuming step of VLDL/LDL component re-isolation, or separation of VLDL or LDL from the 3H-CE containing HDL before the disintegrations per minute (DPM) of 3H-CE transferred can be determined.

The present method does not require the separation of any components of the incubation mixture, nor does the present method use radioactive isotopes.

An article entitled: Cholesteryl Ester Exchange Protein in Human Plasma Isolation and Characterization by N. M. Pattnaik, A. Montes, L. B. Hughes and D. B. Zilversmit, Biochemica et Biophysica Acta 530, pp. 428–438 (1978), discloses a method of activity measurement of CETP that also utilizes radioactive CE in HDL. This method is an improvement over the above method by simplifying the incubation mixture components separation or the re-isolation technique discussed above. In the cited article, separation of the LDL component from the HDL component is accomplished by precipitation of the LDL component of the incubation mixture. The LDL precipitate is pelleted by a relatively short slow-speed centrifugation and the remaining HDL supernatant is counted. The loss of radioactivity from the HDL component is attributed to 3H-CE transferred to the LDL pellet. This method requires the use of radioactive isotopes and it is believed both prior art publications yield poor sensitivity and accuracy, characteristic of methods that require a high incident of sample manipulation.

An article titled: Fluorescent Determination of Cholesteryl Ester Transfer Protein (CETP) Activity in Plasma by N. Dousset, L. Douste-Blazy in Clinical Chemistry, vol. 38, No. 2, p. 306 (1982), is an improvement over previous methods of activity measurement since it discloses a technique that does not require radioactive components. In this method, transfer activity of the CETP is determined by the measurement of transfer of a fluorescent labeled CE. In this reference, the cholesteryl ester molecule utilized as the CETP substrate for transfer has been covalently bound to a fluorescent molecule derived from pyrene. The pyrene labeled cholesteryl ester (PY-CE) is recognized by the CETP and the PY-CE may be detected by a fluorimeter. The accumulation of the PY-CE in the LDL fraction is, however, only able to be determined after the separation of the LDL acceptor from the HDL donor.

An article entitled: Enhancement of The Human Plasma Lipid Transfer Protein Reaction by Apolipoproteins by T. G. Milner, K. W. S. Ko, T. Ohnishi, and S. Yokoyama in Biochimica Biophysica Acta 1082, pp. 71–78 (1991), discloses a method for determining the activity of CETP also utilizing a pyrene labeled CE (PY-CE). This method does not require separation or re-isolation of substrates, but uses the measurement of both monomer and excimer fluorescent emission from the pyrene label to determine a ratio thereof. The cited article is improving upon certain aspects of the previous method. However, the method is based upon excimer to monomer ratio to determine accumulation of PY-CE in the acceptor and does not account for lipoprotein core viscosity changes affecting the excimer to monomer ratio. Pyrene labels have been used extensively in physical biochemistry to study particle core viscosity. This cited method is a technique that results in problems with accuracy as noted in this article. In addition, the method is inconvenient due to oxygen quenching of excimer emission and requires the constant gassing of samples with nitrogen.

An article entitled: Use of Fluorescent Cholesteryl Ester Microemulsions in Cholesteryl Ester Transfer Protein Assays by Charles L. Bisgaier, Laura Minton, Arnold D. Essenberg, Andrew White, and Reynold Homen published in the Journal of Lipid Research, Volume 34, 1993 discloses a method that utilizes a self quenching florescent labeled cholesteryl ester core. The reference cited, although an improvement, does not address the problems associated with emulsion instability and, as pointed out by the authors, spectral interference due to the presence of colored compounds.

An article entitled: Protein Disulfide is a Component of the Microsomal Triglyceride Transfer Protein Complex by Wetterau, J. R.; Combs, K. A.; Spinner, S. N. and Joiner, B. J. discloses a method of measuring MTP activity utilizing radioactive isotopes.

The priority application, noted above, will not be applicable in instances where the addition of colored compounds accompany neutral lipid transfer protein activity measurements.

The present method is readily usable for the purpose of performing simple, rapid and accurate tests to determine activity of CETP or MTP in the presence of compounds that may otherwise prevent accurate measurement. This present method accomplishes this without the use of radioactive substrates, utilizing a stable emulsion substrate without requiring separation of donor and acceptor particles to quantify activity measurements. Further, it yields a real time activity and the reagent substrate emission is not subject to quenching by oxygen. Still further, the fluorescent emission spectra monitoring the enzyme activity is correctable in the event of spectral interference.

SUMMARY OF THE INVENTION

It is a principal object of this invention to provide a method and a device for rapid and accurate determination of CETP or MTP activity utilizing fluorescence, in a sample that would otherwise yield inaccurate results due to spectrally interfering components.

It is another object of the present invention to provide such a method and such a device for individuals in the field for the purpose of determining the relative activity of CETP or MTP in the presence of a potential inhibitor of the transfer activity.

It is still another object of the present invention to provide such a method and such a device that is accurate and without utilization of radioisotopes.

It is yet another object of the present invention to provide such a device that indicates to a physician, from a sample of whole blood, if a patient has high CETP activity so the physician may recommend modification of the patient diet before atherosclerosis is evidenced.

It is a further object of the present invention to provide a new synthetic donor particle that is used in this method and device.

To the accomplishments of the foregoing objects and advantages, the present invention, in brief summary, comprises a device that determines the activity of CETP or MTP by the use of a newly synthesized donor particle without regard to the presence of colored or otherwise interfering factors.

The present invention also includes a method for measuring the activity of cholesteryl ester transfer protein or MTP. The method comprises the steps of: adding a prepared emulsion particle to a buffer to form a buffered solution simulating physiological conditions, and adding an emulsion of lipid to the buffered solution of prepared sonicated particle. The added lipid emulsion acts as an acceptor particle to accept CETP or MTP mediated transfer of a fluorescent neutral lipid such as, NBD-CE or NBD-TG. The acceptor lipid emulsion may be a commercially available preparation, such as that marketed under the trade name "Intralipid". The method also comprises adding a source of CETP or MTP to the buffered solution, and adding a compound to the buffered solution for the purpose of testing the compound's effect on the neutral lipid transfer protein, namely CETP and MTP activity. The CETP source may be normal human plasma. The MTP source may be liver or intestinal cell homogenate. The method further comprises incubating the buffered mixture, reading the fluorescence of the solution, and calculating the effect of the compound on the emission spectra of the transfer label so transfer activity can than be accurately determined.

The present invention includes two species of particles: a donor particle, comprised of a self quenching fluorescent neutral lipid (cholesteryl ester or triglyceride) core, and an acceptor particle, to accept protein facilitated transfer of fluorescent neutral lipid. The present invention also includes means to determine interference on the emission intensity of the fluorescence of the particles.

BRIEF DESCRIPTION OF THE DRAWINGS

The foregoing and still other objects and advantages of the present invention will be more apparent from the following detailed explanation of the preferred embodiments of the invention in connection with the accompanying drawings wherein.

DESCRIPTION OF THE PREFERRED EMBODIMENTS

Figure 1:
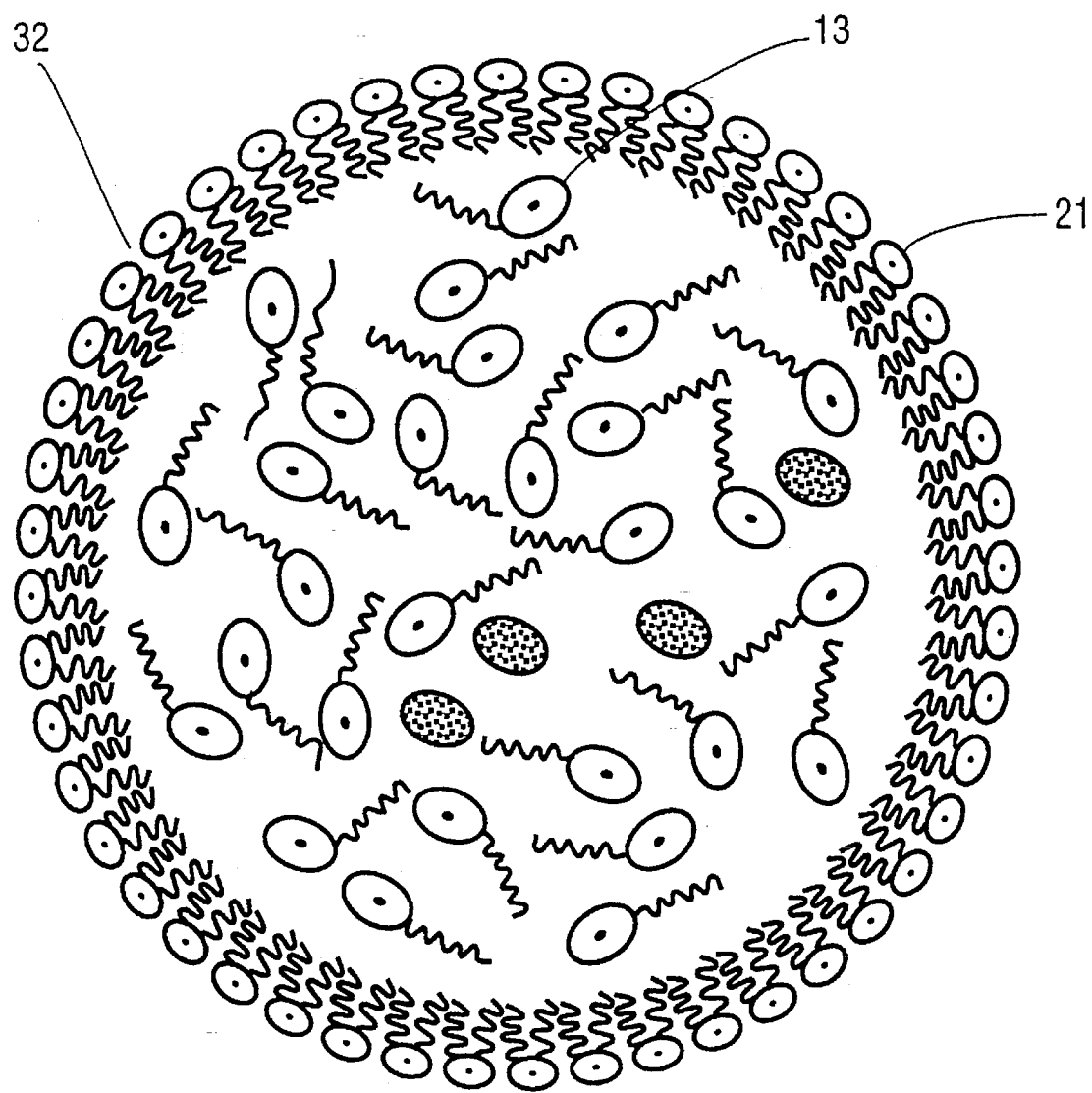
FIG. 1 is a cross section of a synthetic emulsion particle used in the present invention.

Cholesteryl ester transfer protein (CETP) is a protein that may be isolated from the plasma of normal humans. MTP is a protein with activity normally expressed in homogenized liver or intestinal cells. CETP or MTP ligands include two neutrally charged or non-polar lipids, namely cholesteryl esters (CE) and triglycerides (TG).

These hydrophobic, neutral lipids are present within the core of lipoprotein particles, and include but are not limited to: high density lipoprotein (HDL), low density lipoprotein (LDL), intermediate density lipoprotein (IDL) and very low density lipoprotein (VLDL). Most lipoproteins are freely circulating in the plasma. The CETP normally transfers the two neutral lipids CE and TG from one lipoprotein particle, the donor, to another lipoprotein particle, the acceptor. MTP, present in a liver or intestinal cell homogenate, will also transfer neutral lipids among donor and acceptor particles.

The present invention is useful in mass screening projects such as those performed by pharmaceutical companies in search of drug candidates. The problems associated with fluorescent assays include attenuation of the fluorescent emission spectra of the fluorescent label used within the assay by the compound added. The attenuation is not a result that is generated by a potential drug candidate's effect on the enzyme tested, but an effect due to a physical property of the compound tested. For example, a solvent extract of a particular plant may be added to a CETP assay system in a screening program utilizing a fluorescent technique to test for a natural product that inhibits CETP. Plant extracts are usually dark green and the color will affect the emission spectra that is detected by the fluorescence detecting device whether or not other compounds within the extract have any effect upon the CETP activity. This problem is pointed out in the above discussed article by Bisgaier, et al.

The present invention allows a calculable emission spectrum interference correction factor to be derived from the assay system by utilizing an additional fluorescent label or by broadening the bandwidth of the same label.

Application of the present invention to a scheme that incorporates the additional fluorescent label into the assay system involves, in one case, an inert label that will not act as a measurement of enzyme activity nor will the additional label interact with the enzymes, such as CETP or MTP. The additional label will be present in the same system setup to measure activity. However, the label is "inert" with respect to the enzymes. Alternatively, the additional fluorescent label may be bound to a substrate of the enzyme and the label's emission spectrum may also be affected by the enzyme's activity, but the label is bound to the enzyme substrate in a different area. In other words, there may be present in the assay system identical enzyme substrates with identical labels attached to the substrates, yet the labels will be located on different molecular areas of the substrates. The location of the labels must be specified so the emission spectrum of each entity is slightly shifted with respect to the other, thereby broadening the emission spectra or broadening the emission bandwidth. The labels in this scheme are not inert.

Generally, if the label for enzyme activity shares the excitation wavelength of the label used to determine spectral interference, the emission wavelength of the interference label is purposely shifted to discern between two peaks of two labels or, in the case of bandwidth broadening, the two peaks become one wide peak. The interference label is purposely shifted to longer wavelengths than the emission peak of the activity measuring label because the longer wavelengths will be more affected by spectral interference.

Simply stated, the present method provides a screen that locates or screens out inhibitors of CETP or MTP. The present method is, preferably, directed to measuring the activity of the cholesteryl ester transfer protein and MTP. However, the present method, and device, is applicable in any fluorescent measuring method where spectral interference is encountered. Where a fluorescent method will normally have a label to follow enzyme activity, the present method adds an additional label to follow the status of fluorescence efficiency not the activity of a specific enzyme or substrate. This is also true where one label is used in the assay but the bandwidth is broadened and the analysis of the data is used as a means to quantify spectral interference regardless of the type of fluorescence assay, enzyme or label.

In order to provide a complete understanding of the present invention and the various techniques used to implement the present invention, the following examples are presented. The examples provided disclose implementation of the invention at four levels: the donor particle level, the acceptor particle level, the molecular level and the instrument level. In this application, "donor" particle refers to the particle responsible for donating cholesteryl ester to CETP or MTP, and "acceptor" particle refers to the particle in the activity measurement system (assay) responsible for accepting cholesteryl ester from CETP or MTP.

Referring to the figures and, in particular, FIG. 1, a synthetic or synthesized particle 32 is representative of an emulsion. The NBD-labeled neutral lipid NBD-CE 13 contained within the core of the synthetic particle will not yield a substantial fluorescent emission intensity when illuminated with excitation wavelength. Instead, the energy of the excited state is dissipated in radiationless energy transitions upon collision with other NBD-CE molecules. The non-fluorescent loss of energy is dependent upon molecular interactions associated with the core sequestered NBD-neutral lipid.

Figure 2:
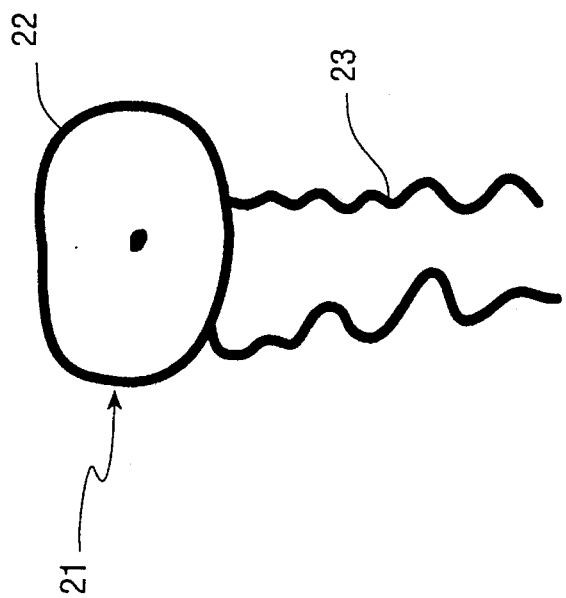
FIG. 2 is an enlarged diagrammatic representation of the phospholipid emulsifier used in the present invention.

The monolayer of PC molecules 21 of FIG. 1, in the synthetic particle 32, is further illustrated in FIG. 2. PC is comprised of a polar head group 22, and non-polar or hydrophobic tail 23. The conditions under which the emulsification process is performed enables the non-polar or hydrophobic tail 23 of the PC molecule to partition with the hydrophobic NBD-neutral lipid, NBD-CE 13 of FIG. 1. The partitioning of hydrophobic constituents of the co-sonication mixture traps the NBD-neutral lipid into a small area relative to the area of the aqueous phase. The PC emulsified NBD-neutral lipid components are in a stable non-aqueous or hydrophobic environment at high concentration with respect to collational proximity and accordingly yield little fluorescence intensity.

According to the present invention, there are several approaches to measure spectral interference so the effect on the enzyme substrate fluorescence may be determined to ultimately give enzyme activity.

APPROACH I

At the donor particle level approach, an inert label is added when the donor particle is synthesized. The inert label is incorporated into the donor particle core by one of the following methods:

METHOD 1

A self-quenching fluorescent neutral lipid, such as NBD-CE 13 of FIG. 1, is emulsified by a suitable emulsifier such as phospholipid, like phosphatidylcholine (PC) 21 of FIG. 2. Although the term emulsify is exemplified by a specific technique below, the present invention is concerned with incorporating the NBD lipid into an emulsified particle efficiently so as to achieve self-quenching emission characteristics of the label. There are many techniques known to emulsify hydrophobic or non-water soluble compounds, such as, NBD-CE or NBD-TG, and many compounds that will act as emulsifying agents.

Figure 3:
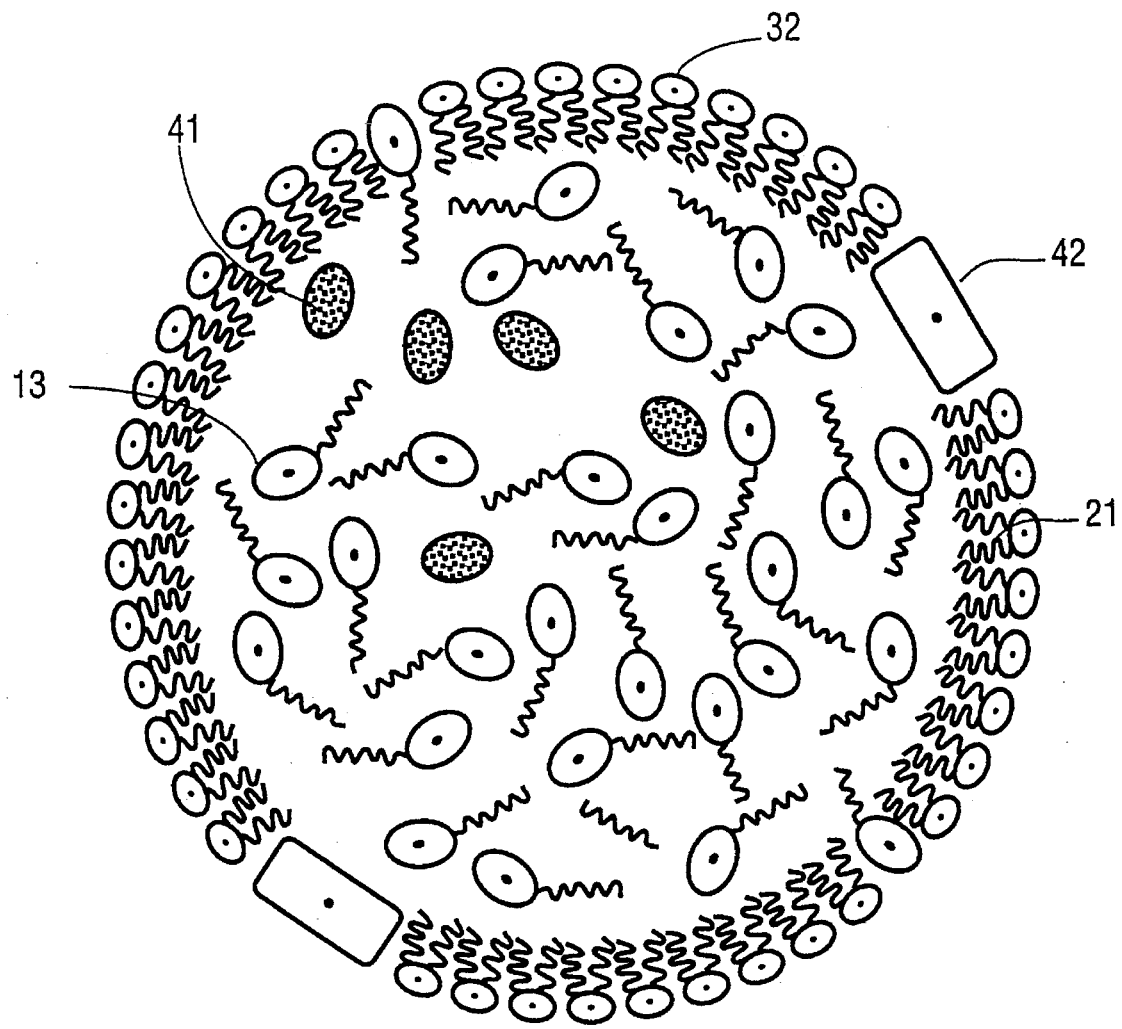
FIG. 3 is a cross section of another synthetic emulsion particle used in the present invention.

Referring to FIG. 3, the emulsion 32, is prepared by sonicating 2.0EE-5 moles of N-(7-nitrobenz-2-oxa-1,3-diazol-4-yl)amino (NBD) labeled neutral lipid (CE or TG) 13, with 13 mg of phospholipid (PL) 21, and 1.0EE-5 moles of anthracenetrinitrobenzene (ATNB) 41, at a power output just under that which causes the sonic probe to cavitate within the sample. A temperature above the melting point of the mixture of component lipids is maintained for 45 minutes in a buffer of 10 ml, 0.1M KCl/10 mM trizma-HCl, pH=8. The sonicated mixture is rapidly cooled to a temperature of 40 degrees centigrade. Ten (10) mg of apolipoprotein apoA-I 42 in 2.5 molar urea is added in less than 1 ml over 15 min. at a sonication power half of that used for the high temperature sonication.

For applications of the present invention requiring a particle similar to HDL, the resulting emulsion is ultracentrifuged at a density of 1.063 g/ml with 1.21 g/ml underlay and a 1.006 g/ml overlay. The HDL density class particle may be harvested from the 1.063 g/ml middle zone. The particle utilizes apolipoprotein apoA-I 42 for stabilization, similar to physiological conditions. Stabilization of the fluorescent donor particle may also be accomplished with synthetic, amino acid peptides.

METHOD 2

Figure 4:
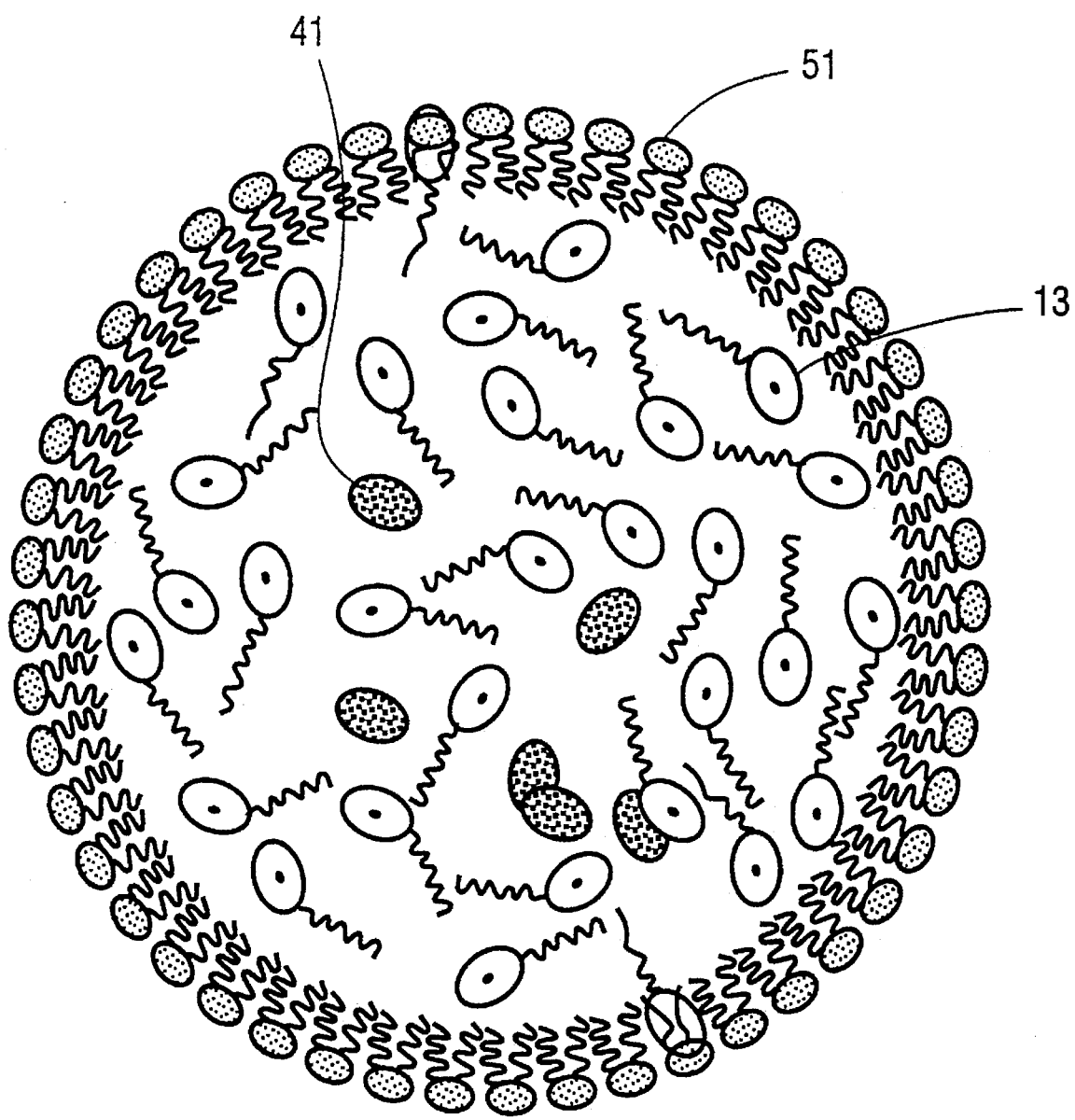
FIG. 4 is a cross section of another synthetic emulsion particle in the present invention.

FIG. 4 shows the particle produced by a second method of fluorescent neutral lipid donor synthesis. It this method, the emulsifier (PC) is replaced by phosphatide (PL) 51 extract. The phosphatide extract is derived from egg yolk or soybean, and includes all phospholipids associated with each source, in particular: lecithin>60%, Phosphatidyl-ethanolamine>15%, lysolecithin<4%. The extract stabilizes the emulsion by providing charged emulsifying phospholipids 51. The charged phospholipids emulsify the fluorescent core comprised of NBD-CE 13, and ATNB 41, producing a net charge associated with each particle. The net charge associated with each particle causes repulsion between the fluorescent donor particles thereby preventing fusion of the particles over time. The apolipoprotein apoA-I of the previous method of donor particle synthesis is eliminated by use of the PL extract. The sonication is performed at 63 degrees centigrade (C) to 68 degrees C. for thirty minutes.

METHOD 3

The third method of an incorporating an interference detection label into the donor particle to measure spectral interference includes utilization of enzyme substrates with labels that are labeled in different molecular locations or the substrates have different labels. The fluorescent emission spectrum of a fluorescent label varies according to the molecular environment of the label. If the NBD label of NBD-CE is covalently bound to the CE in different areas a broader emission band width will result.

METHOD 4

The fourth method of incorporating the interference label into the core of the donor particle includes: injection of 1.0EE-6 moles of ATNB dissolved in 5 microliters of dimethylsulfoxide (DMSO) into 2 ml of prepared donor emulsion. This will be referred to as the DMSO partition method of labeling.

APPROACH II

The second approach utilizes the acceptor particle as the carrier of the inert label:

a. A simple triglyceride emulsion is prepared from 1.0 gm of soybean oil, 0.124 gm of PL, 0.225 gm of glycerine and 1.0EE-5 moles ATNB in 10 ml of distilled water by sonication.

b. ATNB is DMSO partitioned into the core of a TG emulsion.

APPROACH III

The third approach creates a separate particle of solely emulsified, inert label, which would be premixed with the fluorescent cholesteryl ester donor and acceptor or the inert particle is added separately to the assay mixture.

APPROACH IV

The fourth approach presents the inert label to the enzyme assay mixture bound to a solid bead or matrix.

The inert label or the label that will not interact with the enzyme or protein under test must have certain spectral characteristics according to the spectral characteristics of the labeled cholesteryl ester or the substrate of the enzyme under test. For accuracy in determining the spectral interference, the inert label must have an emission maximum of equal or longer wavelength than that of the non-inert, labeled substrate. An inert label with emission maximum at equal or longer wavelengths than the labeled substrate ensures an accurate measurement of spectral interference caused by the colored or otherwise interfering compound. The interference or attenuation of emission energy will be more pronounced at longer wavelengths because the photons are less energetic than photons of shorter wavelength. This will provide a means to quantify with confidence the influence of a colored compound on the fluorescent label involved with enzyme activity. The inert label may have the same or different excitation wavelength. If the inert label has an excitation wavelength that is the same as the enzyme substrate or non-inert label, the emission maximum of the inert label must be shifted toward longer wavelengths. If the excitation wavelength of the inert label is different than that of the substrate or non-inert label the emission maximum of the inert label may be equal to the non-inert label.

The scope of the present invention is not limited to emulsion based assays, such as determination of CETP or MTP activity. However, the prepared emulsions of this invention provide the means for spectral interference correction at the assay component level and many physiological assay systems, currently utilizing radioisotopes could be adapted to fluorescence based systems, most would tolerate spectral interference detection labels.

Figure 5:
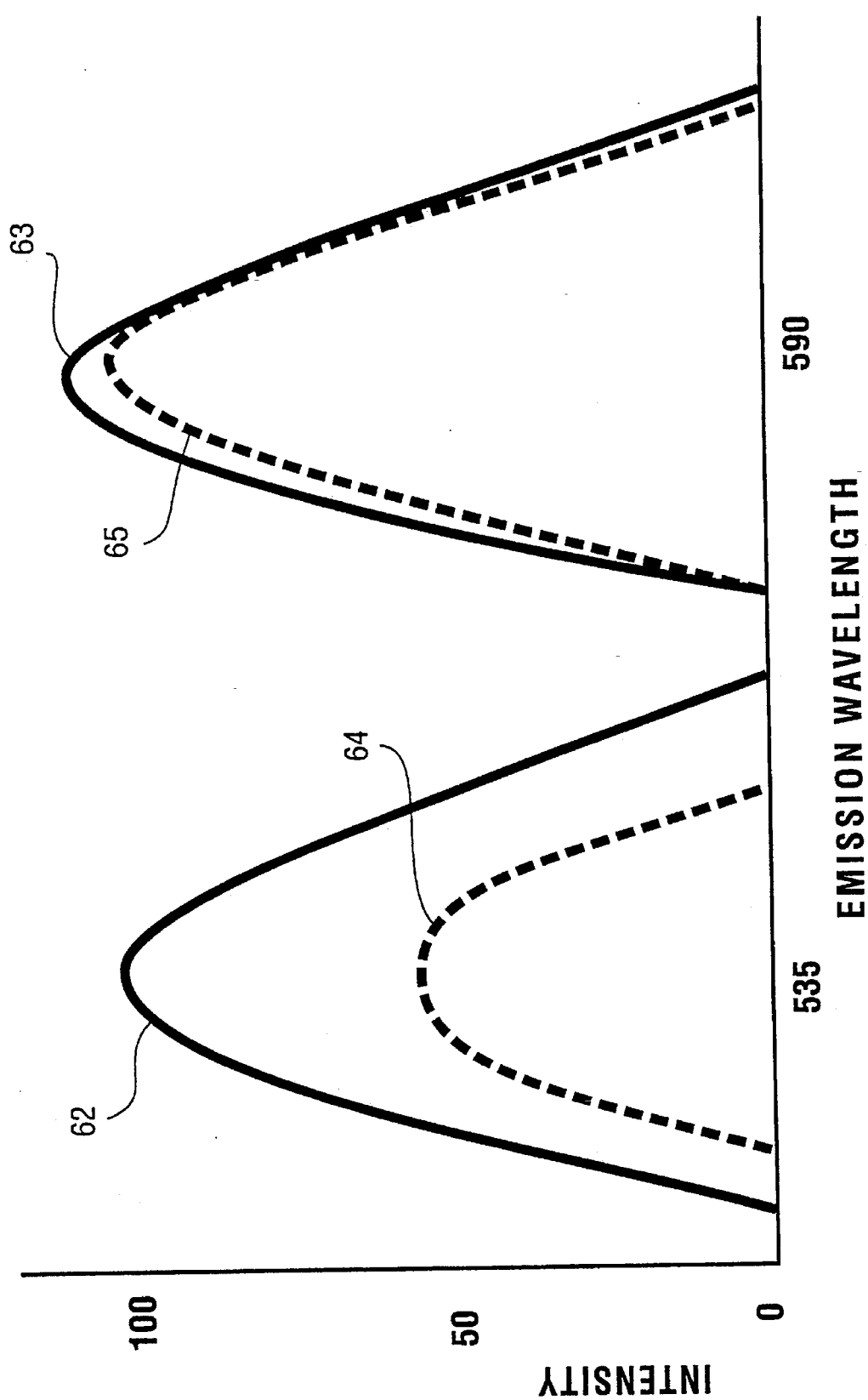
FIG. 5 is a plot of the emission spectra generated from an assay used in the present invention.

Referring to FIG. 5, the NBD-fluorescent label covalently bound to cholesteryl ester of NBD-CE, incorporated into the core of an emulsion particle with ATNB, excited at 465 nm, yields an emission spectra as depicted. The distribution of fluorescent intensity from 500 nm to 600 nm (X-axis) reveals the emission fluorescence intensity (Y-axis) maximum at 535 nm at 62, for the NBD-CE and the emission maximum of the ATNB at 590 nm at 63. The plots of emission intensity 62, 63 represents the results obtained from a control that demonstrates transfer and no disturbance of emission intensity according to the present invention. In FIG. 5, the dotted line 64 and dotted line 65 represent a control without transfer protein added and, accordingly low emission intensity at the 535 nm wavelength. The ATNB emission intensity is unchanged, indicating no spectral interference.

Figure 6:
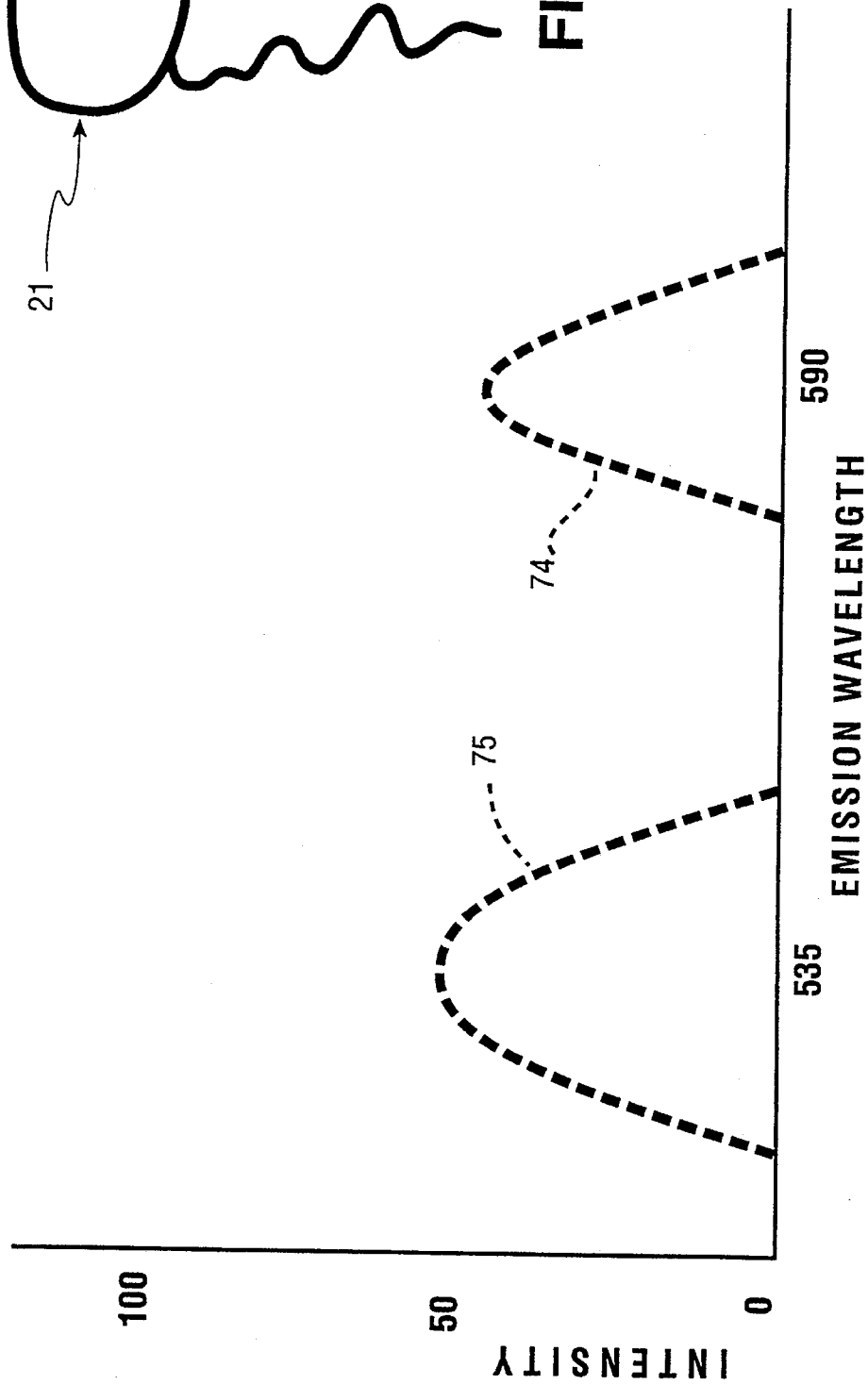
FIG. 6 is a plot of the emission spectra generated from an assay used in the present invention.

FIG. 6 illustrates the result of an interfering or colored compound on the NBD and ATNB emission spectra. The ATNB peak at 74, is approximately 40% of the control and the NBD peak at 75 is approximately 50% of control. This result, without the presence of the ATNB peak, would be falsely interpreted as the IC50 or concentration of inhibitor at 50% inhibition of the enzyme. The emission spectra of the ATNB changes only when the assay is confronted with a colored or otherwise interfering compound, and it is affected to a greater degree than the shorter, more energetic light emitted by the NBD. The NBD label, however, is affected by both transfer protein activity and spectral interference. Applying this concept to an interference detecting label with a different excitation wavelength than the label used to measure transfer protein activity, simply requires the spectra to be collected under each excitation to determine the status of each label.

Those skilled in the art will understand that this technique involves a relationship between emission energy and degree of interference with respect to accuracy desired. Many other combinations of fluorescent label pairs would be sufficient for measurement of spectral interference even those with emission maximums below the label for transfer measurement.

Figure 7A:
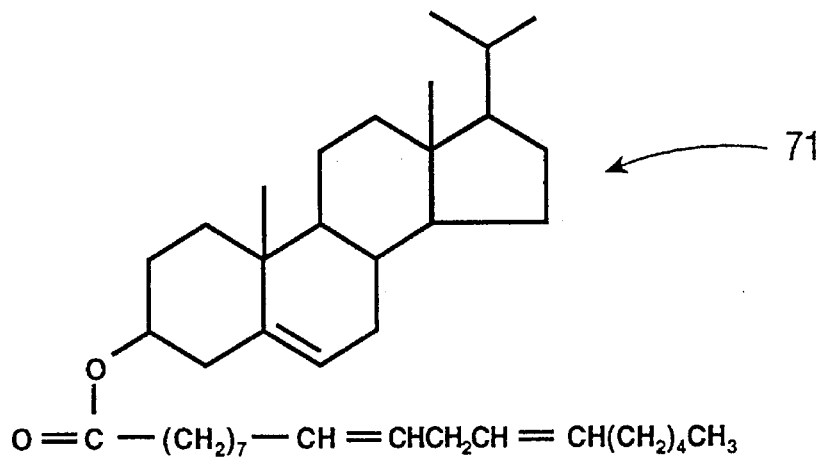
FIG. 7A is a diagram of a cholesteryl ester.
Figure 7B:
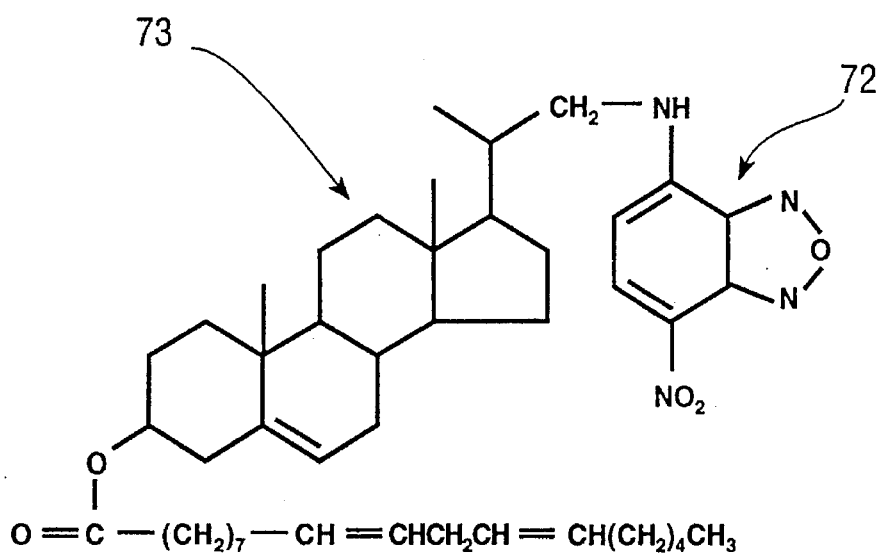
FIG. 7B is a diagram of a NBD fluorescent label chemically bonded to the CE molecule in accordance with present invention.
Figure 7C:
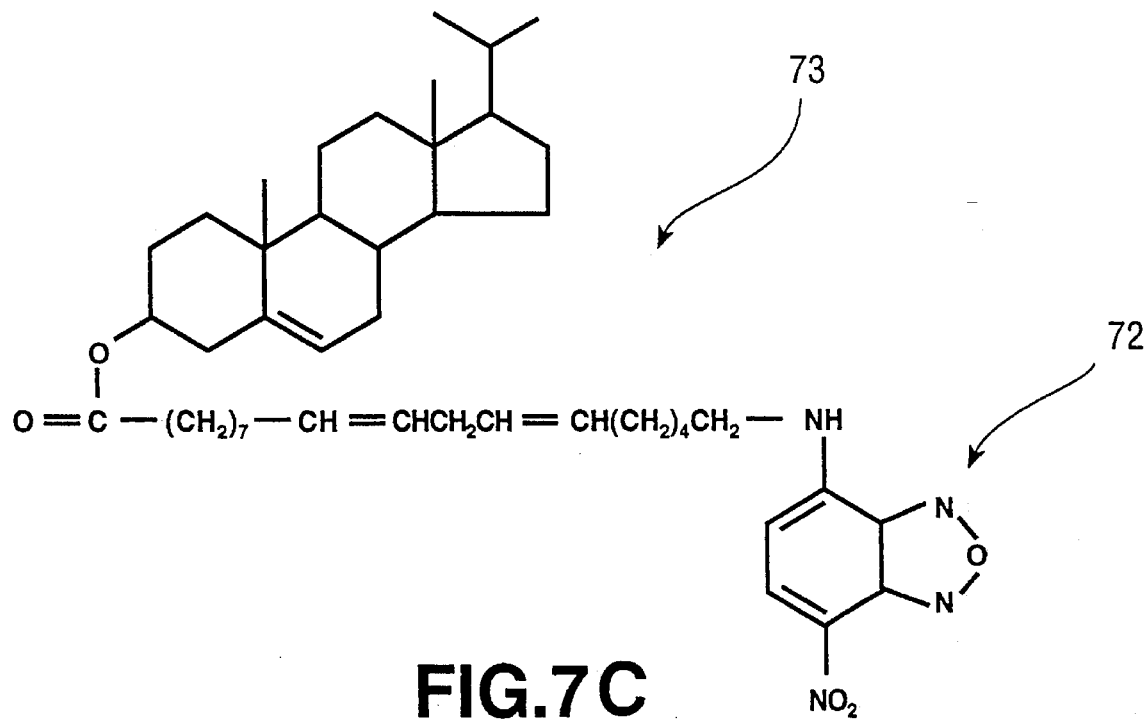
FIG. 7C is a diagram of a variant of the NBD fluorescent label in accordance with the present invention.

The present invention also provides a method of interference detection using one label, yet the label is bound to the same species of substrate in different areas on the substrate molecule. For the sake of illustration, the substrate, cholesteryl ester (CE) 71, is shown structurally in FIG. 7A. The NBD fluorescent label 72 is chemically bonded to different areas of the CE molecule in the formation of the florescent labeled NBD-CE 73 as represented in FIGS. 7B and 7C. The emission spectra of a mixture of these two substrates will be broader than each one studied separately, or one will be of slightly longer wavelengths than the other.

Figure 8:
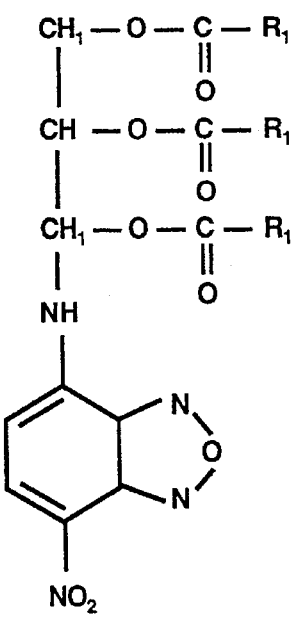
FIG. 8 is a diagram of a NBD labeled TG in accordance with the present invention.

Another method of broadening the emission spectra, according to the present invention is the inclusion of a different substrate of the enzyme in the assay. In the CETP or MTP assay according to the invention, NBD labeled TG is shown in FIG. 8. A mixture of NBD-TG and NBD-CE included in the assay will also broaden the emission spectra of the assay.

The efficiency of fluorescence is determined from the loss of peak broadness as the lower energy (longer wavelength) emission is affected relative to a control. In other words, if an enzyme inhibitor is present in the assay, the bandwidth will be proportional to a control, but the intensity will be less than control. If a compound is interfering with emission efficiency the bandwidth will be disproportionately narrower than control.

Bandwidth broadening by specifying attachment of the label at different points on the substrate molecule exposes the label to alternate molecular environments in the excited state, providing alternate pathways to the ground state, causing spectral shifts in identical substrates.

Having thus described the present invention with particular reference to the preferred forms thereof, it will be obvious that various changes and modifications may be made therein without departing from the spirit and the scope of the present invention as defined by the appended claims.

Wherefore I claim:

1. A fluorescence method for measuring the activity of a neutral lipid transfer protein, the method comprising the steps of:

adding a prepared emulsion particle to a buffer to form a buffered solution, wherein the particle has a core having a neutral lipid with a self quenching label emitting electromagnetic radiation at a first wavelength;

adding a lipid emulsion to the buffered solution;

adding a source of neutral lipid transfer protein to the buffered solution;

incubating the buffered solution to obtain an incubated solution; and, reading the fluorescence of the incubated solution.

2. The method of claim 1 in which the self quenching label is N-(7-nitrobenz-2-oxa-1,3-diazol-4-yl)amino (NBD).

3. The method of claim 1 further comprising the step of adding a test compound to the buffered solution for the purpose of testing the effect of the compound on the transfer protein activity.

4. The method of claim 3, further comprising the steps of calculating from the fluorescence reading of the incubated sample and a fluorescence reading of the inert compound the effect of the test compound on the emission spectra of the label to determine the effect of the test compound on the label fluorescence, whereby the effect of the test compound on the neutral lipid transfer protein is determined.

5. The method of claim 3 in which the core of the emulsion particle further comprises an inert compound emitting electromagnetic radiation at a wavelength other than the first wavelength.

6. The method according to claim 1, wherein the neutral lipid transfer protein is cholesteryl ester transfer protein CEPT).

7. The method according to claim 1, wherein the neutral lipid transfer protein is microsomal transfer protein.

8. The method according to claim 1, wherein the method incorporates an additional label that follows the status of fluorescence efficiency.

9. The method according to claim 1, wherein the source is added to the buffered solution after the lipid emulsion has been added.

10. The method according to claim 1, wherein the compound is added to the buffered solution after the lipid emulsion and the source have been added.

11. The method according to claim 1, wherein the added lipid emulsion acts as an acceptor particle to accept a neutral lipid from either a cholesteryl ester transfer protein source or a microsomal transfer protein source.

12. The method according to claim 11, in which the neutral lipid is selected from the group consisting of N-(7-nitrobenz-2-oxa-1,3-diazol-4-yl)amino -cholesteryl ester (NBD-CE) and N-(7-nitrobenz-2-oxa-1,3-diazol-4-yl) amino-triglyceride (NBD-TG).

13. The method according to claim 11, wherein the cholesteryl ester transfer protein source is normal human plasma.

14. The method according to claim 11, in which the microsomal transfer protein source is selected from the group consisting of liver cell homogenate, intestinal cell homogenate, or derivatives thereof.

15. The method of claim 6 in which the activity level of CETP as measured by the fluorescence of the incubated sample is indicative of a risk factor for atherosclerosis.

16. The method of claim 1 in which the source is human plasma.

17. The method of claim 15 in which the human plasma has a naturally occurring concentration of neutral lipid transfer protein.

18. A device that determines the activity of a neutral lipid transfer protein by the use of a newly synthesized donor particle without regard to the presence of colored and other spectral interference factors comprising:

a first fluorescence indicator having an intensity that is measured to determine the activity of said protein and emitting electromagnetic energy at a first wavelength; and, a second fluorescence indicator having a second intensity that is measured to determine spectral interference affecting the first fluorescence indicator intensity and emitting electromagnetic energy at a second wavelength, whereby the fluorescence intensities of the first indicator and the second indicator are measured under the same conditions with only the first fluorescent indicator intensity affected by both protein activity and spectral interference.

19. The device according to claim 18, wherein the neutral lipid transfer protein is a cholesteryl ester transfer protein.

20. The device according to claim 18, wherein the neutral lipid transfer protein is a microsomal transfer protein.

21. A donor particle comprising a self quenching fluorescent neutral lipid core, said core having components therein emitting electromagnetic radiation at a first wavelength, and said core comprising cholesteryl esters, triglycerides, and derivatives thereof; and, a fluorescent label emitting electromagnetic radiation at a wavelength other than said first wavelength.

22. The donor particle according to claim 21, in which the fluorescent label is inert.

23. The donor particle according to claim 21, in which the fluorescent label is bound to a substrate of a transfer protein, and the label is not inert.

24. A system for correcting for spectral interference of a spectrally interfering compound, comprising:

a donor particle comprising a self quenching fluorescent neutral lipid core, said core having at least a fluorescently labeled lipid emitting electromagnetic radiation at a first wavelength, said lipid selected from the group consisting of cholesteryl esters, triglycerides, and derivatives thereof;

an acceptor particle for accepting protein facilitated transfer of fluorescent neutral lipid from said donor particle;

a fluorescently labeled compound emitting electromagnetic radiation at a wavelength other than the first wavelength to assist in the determination of the interference of spectrally interfering compound; and, means to determine interference of the spectrally interfering compound on the emission intensity of the fluorescence of the particles.

25. A method of facilitating and simplifying the measurement of neutral lipid transfer protein activity comprising the steps of:

measuring fluorescence of a neutral lipid transfer protein assay system with an instrument to obtain a fluorescence activity measurement;

determining an emission spectral interference factor from the neutral lipid transfer protein assay system; and, utilizing the interference factor to correct for a distortion of the fluorescence activity measurement.

26. A method of facilitating and simplifying the measurement of the activity of an enzyme comprising the steps of:

interacting a first fluorescently labeled substrate with an emission intensity dependent on the enzyme's activity with the enzyme;

interacting a fluorescently labeled component with an emission intensity independent of the enzyme's activity with the enzyme;

measuring an emission intensity of the fluorescently labeled component with an instrument to obtain a spectral interference value;

measuring an emission intensity of the first fluorescently labeled substrate with an instrument to obtain an uncompensated emission intensity value; and, subtracting the uncompensated emission intensity value from the spectral interference value to obtain a compensated enzyme activity reading.

27. A kit used to measure an enzyme's activity, comprising;

a first fluorescent component with a fluorescence emission intensity dependent on the enzyme's activity; and, a second fluorescent component with a fluorescence emission intensity independent of the enzyme's activity.

28. The kit of claim 27 in which the first fluorescent component is selected from the group consisting of an emulsified fluorescent labeled enzyme substrate and an emulsified non-fluorescent labeled enzyme substrate.

29. The kit of claim 27 in which the second fluorescent component is an emulsified antracenetrinitrobenzene, or derivatives thereof.

30. The kit of claim 27 further comprising a spectrally interfering component.

31. The kit of claim 27 further comprising an inhibitor of the enzyme.

32. The kit of claim 27 in which the enzyme is selected from the group consisting of CETP and MTP.

33. A method for measuring the activity of neutral lipid transfer protein utilizing fluorescence, comprising the steps of:

preparing a donor particle having a first fluorescently labeled lipid emitting electromagnetic radiation at a first wavelength; and a second fluorescently labeled compound emitting electromagnetic radiation at a wavelength other than said first wavelength to obtain a donor particle mixture;

adding the donor particle mixture to an acceptor emulsion utilizing neutral lipid to obtain an intermediate emulsion:

adding a spectrally interfering compound to the intermediate emulsion to obtain a spectrally interfering emulsion;

adding a source of neutral lipid transfer protein to the spectrally interfering emulsion to obtain a source containing emulsion;

determining the fluorescence intensity of the first fluorescently labeled lipid;

determining the fluorescence intensity of the second fluorescently labeled compound; and, determining the effect of the spectrally interfering compound on the first fluorescently labeled lipid fluorescence by measuring a loss of fluorescence intensity due to spectral interference of the spectrally interfering compound.

34. The method of claim 2 further comprising the step of incubating the source containing emulsion.

35. The method of claim 33 in which the donor particle comprises the second fluorescently labeled compound.

36. The method of claim 32 in which the second fluorescently labeled compound is outside the donor particle.

37. The method of claim 32 in which the acceptor emulsion comprises the second fluorescently labeled compound.

38. The method of claim 32 in which the second fluorescently labeled compound is bound to a constituent selected from the group comprising a bead, an inert substrate, and a matrix.

39. The method of claim 32 in which the second fluorescently labeled compound has an excitation wavelength about the same as an excitation wavelength of the first fluorescently labeled lipid and in which an emission maximum of the second fluorescently labeled compound is at a wavelength other than the first fluorescently labeled compound.

* * * * *